(12) United States Patent
Chen et al.

(10) Patent No.: US 12,171,880 B2
(45) Date of Patent: Dec. 24, 2024

(54) METFORMIN TABLET FOR RELIEVING PAIN AND REDUCING INFLAMMATION AND MANUFACTURING METHOD THEREOF

(71) Applicant: Taiwan Mercury Medical Corporation, New Taipei (TW)

(72) Inventors: Chao-Yi Chen, New Taipei (TW); Chih-Chia Tsai, New Taipei (TW)

(73) Assignee: Taiwan Mercury Medical Corporation, New Taipei (TW)

( * ) Notice: Subject to any disclaimer, the term of this patent is extended or adjusted under 35 U.S.C. 154(b) by 0 days.

(21) Appl. No.: 17/940,746

(22) Filed: Sep. 8, 2022

(65) Prior Publication Data
US 2024/0082163 A1    Mar. 14, 2024

(51) Int. Cl.
*A61K 9/20*    (2006.01)
*A61K 9/00*    (2006.01)

(52) U.S. Cl.
CPC .......... *A61K 9/2054* (2013.01); *A61K 9/0056* (2013.01); *A61K 9/2009* (2013.01); *A61K 9/2018* (2013.01); *A61K 9/2036* (2013.01); *A61K 9/2077* (2013.01)

(58) Field of Classification Search
CPC .. A61K 9/2054; A61K 9/0056; A61K 9/2009; A61K 9/2018; A61K 9/2036; A61K 9/2077; A61K 9/2072; A61K 9/2095
See application file for complete search history.

(56) References Cited

U.S. PATENT DOCUMENTS

| 2016/0206557 A1* | 7/2016 | Liu | A61K 9/2004 |
| 2019/0231850 A1* | 8/2019 | Acosta | A61K 47/10 |
| 2022/0054409 A1* | 2/2022 | Yoo | A61K 9/2054 |

OTHER PUBLICATIONS

CD Formulation (Carrier Excipients) (Year: 2023).*
AZO Materials (Porosity and its Influence on Pharmaceutical Tablet Dissolution, Feb. 14, 2017) (Year: 2017).*

* cited by examiner

*Primary Examiner* — Lezah Roberts
*Assistant Examiner* — Abdulrahman Abbas
(74) *Attorney, Agent, or Firm* — Ying-Ting Chen; Law Office of Michael Chen

(57) ABSTRACT

A metformin tablet, a metformin tablet for relieving pain and reducing inflammation, and a manufacturing method thereof. The tablet for relieving pain and reducing inflammation comprises: a filler, a diluent, an excipient, a binder, a slow-release agent, a sweetener, and a medicinal powder; the excipient comprises: at least one of PVP, PEG, and polymer; the medicinal powder comprises: at least one of metformin and the excipient. The metformin tablet comprises: a hollow part, a thick colloidal layer formed on an outer side of the hollow part, and a powder colloidal layer formed on an outer side of the thick colloidal layer. The tablet for relieving pain and reducing inflammation comprises: a thick colloidal layer, a powder colloidal layer formed on an outer side of the thick colloidal layer, and a hollow part located at a center of the tablet and on an inner side of the thick colloidal layer.

1 Claim, 2 Drawing Sheets

METFORMIN TABLET FOR RELIEVING PAIN AND REDUCING INFLAMMATION AND MANUFACTURING METHOD THEREOF

BACKGROUND OF THE INVENTION

Field of Invention

The invention relates to a metformin tablet for relieving pain and reducing inflammation; the metformin table; and a manufacturing method thereof; and more particularly to a metformin tablet for relieving pain and reducing inflammation of a hollow structure comprising a hollow part, a thick colloidal layer and a powder colloidal layer; a composition for forming the metformin tablet; and a manufacturing method for preparing the metformin tablet.

Related Art

Metformin is an oral hypoglycemic drug which is relatively safe and has a long history. It belongs to biguanide hypoglycemic drugs and is the first choice for diabetic patients. Its mechanism is converted into an AMPK activator and is expected to bring analgesic effect. Metformin is commonly used in Uformin, Glucophage, Loditon, and Glibudon. Metformin is capable of reducing blood sugar by reducing the amount of glucose produced by the liver, reducing the absorption of glucose in the intestine, and increasing the utilization of sugar by the human body. Metformin is also capable of increasing the sensitivity of cells to insulin to increase the efficiency of the body in using insulin; that is, metformin is capable of reducing the production of new glucose, improving an effect of insulin on old glucose, and achieving an effect of lowering blood sugar.

Metformin is mainly metabolized by the kidneys, so it is very important to check the kidney function regularly before and during the use of the drug. In addition, the main effect of metformin is in the gastrointestinal tract, so diarrhea, indigestion, and flatulence are the most common side effects or adverse reactions. Also, taking metformin can have a very low chance of causing the rare side effect of "lactic acidosis". According to the records of the drug instructions list approved by the Ministry of Health and Welfare in Taiwan, taking metformin will have a risk of about 3 in 100,000 chance causing "lactic acidosis".

It is worth noting that lactic acidosis is a rare and serious adverse reaction of metformin, although the probability is extremely low, half of the patients die because of it, mostly patients with kidney function insufficiency. The so-called "lactic acidosis" refers to the amount of lactic acid produced by the human body is greater than the rate of metabolism, resulting in a large accumulation of lactic acid in the blood. Common symptoms include fatigue and lethargy, general weakness, muscle pain, difficulty in breathing, chills, dizziness, and gastrointestinal discomfort; in severe cases, there may even be fatal crises such as disturbance of consciousness, decreased blood pressure, slow heartbeat, and coma.

The current starting dose of metformin is 500 mg 2-3 times a day. Maximum daily dose of metformin: 3000 mg. Metformin therapy is not recommended for elderly patients over 80 years of age. Since it is mainly metabolized by the kidneys, it cannot be used by people with poor renal function. In addition, advanced age, patients or people with heart failure, poor lung and liver function, severe infection, dehydration, alcoholism, and concomitant use of developer (within two days) will increase the risk of lactic acidosis, and are also contraindicated for metformin.

In addition, metformin is a highly water-soluble drug with poor flow and compressibility characteristics, therefore, it cannot be compressed in its purified form; and because it is a high-dose drug, it tends to end-block during tablet production, which may result in yield loss and quality damage. In order to improve flowability and compressibility, the prior art suggests using a method of mixing metformin with a special excipient of specific particle size and density ranges, and then directly compressing the mixture; or using a method in which a granular product is formed by a slow-release agent formed of granular metformin and a hydrocolloid with an aqueous solvent, and then the granular product is dried to reduce the residual moisture content. However, the use of excipient in specific particle size and density ranges results in a tedious and complex preparation process; thus, resulting in increased manufacturing costs.

In addition, it has also been proposed to use a single granular form containing metformin and a slow-release substance to form the inner solid granular phase, to mix the single granule forming the inner solid granular phase with the outer solid continuous phase containing the slow-release substance, and the particles of the inner solid granular phase are dispersed and embedded in the outer solid continuous phase. Wet granulation of metformin and the slow-release substance is used with an aqueous or organic solvent to make the inner granular phase. The inner granular phase is subsequently dried and mixed with the outer continuous phase and compressed into a tablet. However, most hydrophilic polymers often react with aqueous systems, causing difficulties in wet granulation, even affecting release characteristics, and various problems such as solvent residues are produced when organic solvents are used.

Therefore, the industry is eagerly looking forward to developing a metformin tablet for relieving pain and reducing inflammation and a manufacturing method thereof capable of solving the above-mentioned various problems in the prior art.

SUMMARY OF THE INVENTION

Therefore, in order to solve the various problems of the above-mentioned prior art, the inventor has devoted to research and develop a metformin tablet for relieving pain and reducing inflammation, a composition for forming the metformin tablet, and a manufacturing method for preparing the metformin tablet.

In other words, an object of the invention is to provide a metformin tablet for relieving pain and reducing inflammation, and a composition for forming the same and a manufacturing method thereof, in addition to being capable of making the tablet smaller by mouth-dissolving before entering a gastrointestinal tract and providing required slow-release properties, also capable of enhancing an activation effect of AMPK, reducing a dosage, and reducing fluctuation of blood sugar in a patient, thereby enhancing a pain relief effect.

In order to achieve the above object, the invention provides a metformin tablet comprising: a filler, a diluent, an excipient, a binder, a slow-release agent, a sweetener, and a medicinal powder; wherein the filler is selected from at least one of microcrystalline cellulose and silicified microcrystalline cellulose; the diluent is selected from at least one of mannitol and sugar alcohol; the excipient is selected from at least one of PVP, PEG and polymer; the binder is selected from at least one of glucose and lactose; the slow-release agent is selected from at least one of polylactic acids; the sweetener is selected from at least one of isomalt; and the medicinal powder is selected from at least one of metformin and its excipient; the metformin tablet comprises: a hollow part, a thick colloidal layer formed on an outer side of the hollow part, and a powder colloidal layer formed on an outer side of the thick colloidal layer.

Optionally, in the metformin tablet of the invention, the thick colloidal layer of the tablet is composed of a mixture of the filler, the diluent, the excipient, the binder, the slow-release agent, and the sweetener.

Optionally, in the metformin tablet of the invention, wherein the thick colloidal layer is composed of a mixture of the filler accounting for 2~22%, the diluent accounting for 3~24%, the excipient accounting for 1~25%, the binder accounting for 0.5~18%, the slow-release agent accounting for 0.1~12%, and the sweetener accounting for 1~22%.

Optionally, in the metformin tablet of the invention, the powder colloidal layer of the tablet is composed of a mixture of the filler, the diluent, the excipient, the binder, the slow-release agent, the sweetener, and the medicinal powder.

Optionally, in the metformin tablet of the invention, wherein the powder colloidal layer is composed of a mixture of the filler accounting for 2~22%, the diluent accounting for 3~24%, the excipient accounting for 1~25%, the binder accounting for 0.5~18%, the slow-release agent accounting for 0.1~12%, the sweetener accounting for 1~22%, and the medicinal powder.

Optionally, in the metformin tablet of the invention, further comprising at least one of disintegrant and lubricant.

Also, in order to achieve the above object, the invention further provides a metformin tablet for relieving pain and reducing inflammation, which comprises: a thick colloidal layer, a powder colloidal layer formed on an outer side of the thick colloidal layer, and a hollow part located at a center of the tablet and on an inner side of the thick colloidal layer; wherein the thick colloidal layer is composed of a mixture of a filler, a diluent, an excipient, a binder, a slow-release agent, and a sweetener; the excipient comprises at least one of PVP, PEG, and polymer; the medicinal powder comprises at least one of metformin and its excipient.

Also, optionally, in the metformin tablet for relieving pain and reducing inflammation of the invention, a colloidal thickness of the thick colloidal layer is greater than a colloidal thickness of the powder colloidal layer.

Also, optionally, in the metformin tablet for relieving pain and reducing inflammation of the invention, a colloidal porosity of the thick colloidal layer is smaller than a colloidal porosity of the powder colloidal layer.

Also, optionally, in the metformin tablet for relieving pain and reducing inflammation of the invention, a surface layer of the tablet has an indentation for folding into two halves.

In addition, in order to achieve the above object, the invention further provides a manufacturing method of a metformin tablet for relieving pain and reducing inflammation comprising step A: on a tablet forming platform, sprinkling a medicinal powder containing an excipient and metformin through a powder dispensing structure; step B: spraying a colloidal composition by a first nozzle to form a powder colloidal layer on a periphery of a thick colloidal layer; and step C: spraying a colloidal composition by a second nozzle to form the thick colloidal layer on a periphery of a hollow part; forming the hollow part located at a center of the tablet and on an inner side of the thick colloidal layer; wherein the excipient comprises at least one of PVP, PEG, and polymer; the medicinal powder comprises at least one of metformin and its excipient; the step A, the step B, and the step C are performed cyclically through the above method according to a required drug dosage.

In addition, optionally, in the manufacturing method of the metformin tablet for relieving pain and reducing inflammation of the invention, the first nozzle and the second nozzle spray to form the thick colloidal layer and the powder colloidal layer respectively by surrounding a center of the hollow part in a swirl manner.

In addition, optionally, in the manufacturing method of the metformin tablet for relieving pain and reducing inflammation of the invention, a hole diameter of the first nozzle is smaller than a hole diameter of the second nozzle.

According to a technical idea of the invention, not only can a dose of metformin be reduced to reduce an impact on blood sugar fluctuations, but also an excellent effect of allowing patients with poor renal function to use the metformin tablet for relieving pain and reducing inflammation of the invention with peace of mind can be achieved. Furthermore, in addition to being capable of making the tablet smaller by mouth-dissolving before entering a gastrointestinal tract and providing required slow-release properties, the metformin tablet for relieving pain and reducing inflammation of the invention is also capable of enhancing an activation effect of AMPK, reducing a dosage, and reducing fluctuation of blood sugar in a patient, thereby enhancing a pain relief effect.

DETAILED DESCRIPTION OF THE INVENTION

Figure 1:
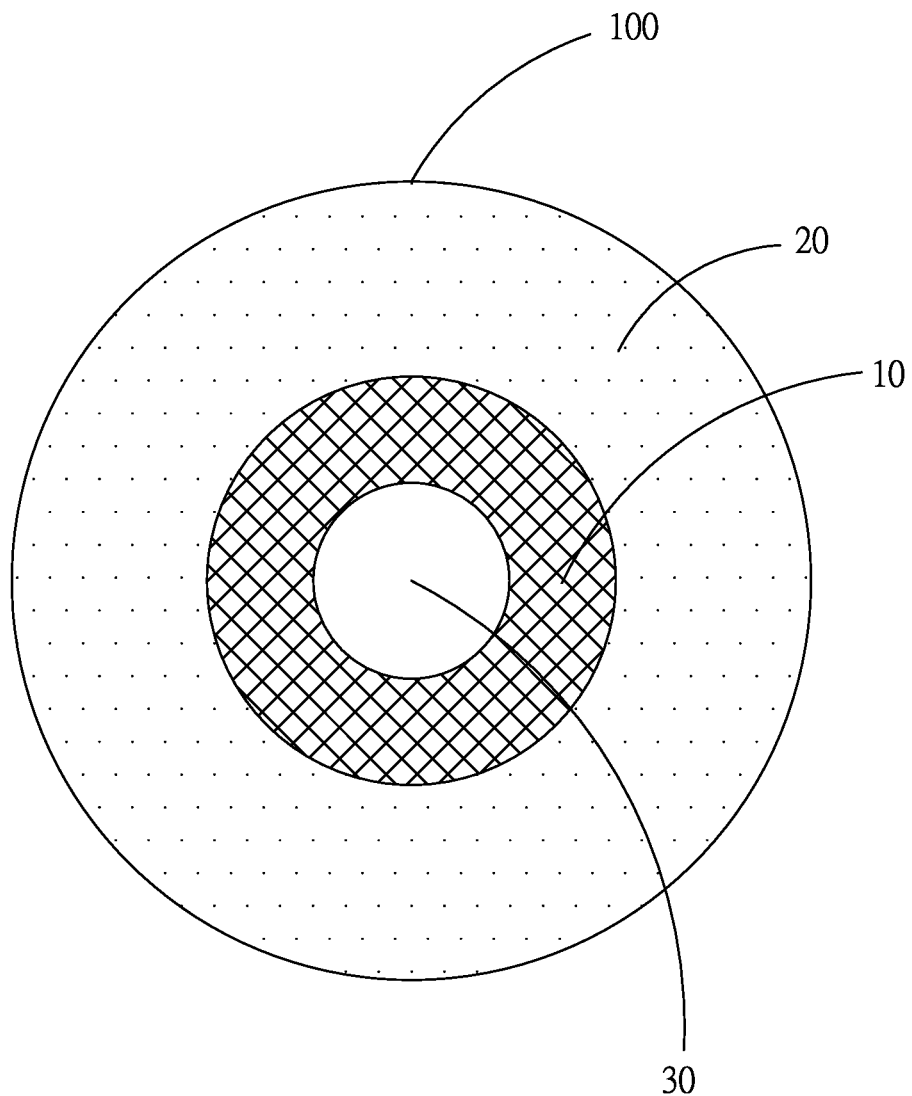
FIG. 1 is a schematic diagram showing a structure of a metformin tablet for relieving pain and reducing inflammation according to one embodiment of the invention.

Each embodiment of the following description has one technical feature or more than one technical feature, but this does not mean that a person using the invention must implement all the technical features in any embodiment at the same time, or can only implement some or all of the technical features in the different embodiments separately. In other words, under the premise of feasible implementation, those skilled in the art can optionally implement some or all of the technical features in any embodiment, or optionally implement a combination of some or all of the technical features in multiple embodiments according to the disclosure of the invention and depending on design specifications or implementation requirements, thereby increasing a flexibility of implementation of the invention.

As used in this specification, the singular forms "a," "an," "one" and "the" comprise plural referents, and the plural form "a plurality" comprises two or more referents unless the content clearly dictates otherwise. As used in this specification, the term "or" is generally employed in its sense including "and/or" unless the content clearly dictates otherwise, and the term is to be construed broadly. For a person having ordinary skill in the art, the specific meanings of the above terms in the invention can be understood according to specific situations.

Although the numerical ranges and parameters defining the broader scope of the invention are approximations, the numerical values set forth in the specific embodiments are reported as precisely as possible. Any numerical value, however, inherently contains the standard deviation resulting from individual testing methods unavoidably. As used herein, "about", "approximately" generally mean that the actual numerical value is within plus or minus 10%, 5%, 1%, or 0.5% of a particular numerical value or range. Alternatively, "about", "approximately" mean that the actual numerical value lies within an acceptable standard error of the average value, depending on the consideration of a person having ordinary skill in the art to which the invention pertains.

In addition to the embodiments, or unless expressly stated otherwise, all ranges, amounts, numerical values and percentages used herein (e.g., used to describe material amounts, lengths of time, temperatures, operating conditions, quantitative ratios, and the like) are understood to be modified by "about", "approximately". Therefore, unless otherwise stated to the contrary, the numerical parameters disclosed in this specification and the accompanying claims are approximate numerical values and can be changed as required. At a minimum, these numerical parameters should be construed as the significant digits indicated and the numerical values obtained by applying ordinary carry method.

In order to make the description of the disclosure more detailed and complete, the following provides an illustrative description of the embodied modes and specific embodiments of the invention; but it is not the only form of implementing or using the specific embodiments of the invention. The features of various specific embodiments as well as method steps and sequences for constructing and operating these specific embodiments are encompassed in the embodied modes. However, other embodiments can also be utilized to achieve the same or equivalent functions and sequences of steps.

Firstly, a metformin tablet for relieving pain and reducing inflammation of the invention will be described. Please refer to FIG. 1 for a schematic diagram showing a structure of the metformin tablet for relieving pain and reducing inflammation according to one embodiment of the invention.

As shown in FIG. 1, a metformin tablet 100 for relieving pain and reducing inflammation according to one embodiment of the invention comprises a thick colloidal layer 10, a powder colloidal layer 20 formed on an outer side of the thick colloidal layer 10, and a hollow part 30 located at a center of the tablet 100 and on an inner side of the thick colloidal layer 10.

According to a technical idea of the invention, the metformin tablet 100 for relieving pain and reducing inflammation of the invention has a specific adhesive ratio, and has a hollow tablet structure of the hollow part 30 formed by an annular colloid sprayed circularly or elliptically in a regular manner according to a fixed or an unfixed tapering or increasing manner. Therefore, the metformin tablet 100 does not cause fluctuations in blood glucose level and plasma insulin level and an effect of rapid pain relief can be achieved.

In addition, in one embodiment of the invention, the thick colloidal layer 10 is composed of a mixture of a filler, a diluent, an excipient, a binder, a slow-release agent, a sweetener, and a medicinal powder; the excipient comprises at least one of PVP, PEG, and polymer; the medicinal powder comprises at least one of metformin and its excipient.

Furthermore, the metformin tablet 100 for relieving pain and reducing inflammation of the invention utilizes a specific binder to stack and bond metformin with powder in certain proportions; thus, the tablet structure can be made looser than the general conventional drugs; in addition, because the metformin tablet 100 is made with a unique pore size, the metformin tablet 100 is capable of increasing a surface area of the tablet, increasing an absorption rate, and speeding up a drug acting time, thereby achieving an effect of rapid pain relief.

Furthermore, in one embodiment of the invention, in addition to the conventional swallowing dosage form, the metformin tablet 100 for relieving pain and reducing inflammation of the invention is preferably in a mouth-dissolving dosage form, thereby improving the convenience of taking the metformin tablet 100.

Furthermore, in one embodiment of the invention, a colloidal ratio of the medicinal powder to the thick colloidal layer 10 and the powder colloidal layer 20 is 1:3~1:20.

Furthermore, a composition of colloid used in one embodiment of the invention, for example, can be composed of a mixture of 1~22% microcrystalline cellulose, 1~24% lactose, 0.5~25% sugar alcohol, 0.5~18% polymers such as PVP and PEG, 0.1~12% polylactic acid, and 1~22% isomalt.

Furthermore, in one embodiment of the invention, a colloidal thickness of the thick colloidal layer 10 is greater than a colloidal thickness of the powder colloidal layer 20.

Furthermore, in one embodiment of the invention, a surface layer of the tablet 100 can have an indentation for folding into two halves.

Then, the metformin tablet 100 of the invention will be described. In one embodiment of the invention, the metformin tablet 100 can be composed of, for example, a filler, a diluent, an excipient, a binder, a slow-release agent, a sweetener, and a medicinal powder.

In one embodiment of the invention, a composition of the medicinal powder in the metformin tablet 100 of the invention, for example, can be composed of a mixture of metformin hydrochloride, alcohol 95%, 2,6-butylated hydroxytoluene, colloidal silicon dioxide, hydroxypropyl cellulose (HPC-EF), magnesium aluminosilicate, microcrystalline cellulose, polyethylene glycol 4000 (PEG 4000), polyethylene oxide (Polyox WSR N-303), polyvinylpyrrolidone K-90 (PVP K90), sodium lauryl sulfate (SLS, SDS); lauryl sodium sulfate, sodium carboxymethyl starch; sodium starch glycolate, titanium dioxide.

According to a technical idea of the invention, the filler is selected from at least one of microcrystalline cellulose and silicified microcrystalline cellulose.

According to a technical idea of the invention, the diluent is selected from at least one of mannitol and sugar alcohol.

According to a technical idea of the invention, the excipient is selected from at least one of PVP, PEG, and polymer.

According to a technical idea of the invention, the binder is selected from at least one of glucose and lactose. In addition, in one embodiment of the invention, the binder can further contain isomalt with hydrolysis rate and absorption rate slower than those of sucrose in order to avoid causing fluctuations in blood glucose level and plasma insulin level and to achieve an effect of rapid pain relief.

According to a technical idea of the invention, the slow-release agent is selected from at least one of polylactic acids; the sweetener is selected from at least one of isomalt.

According to a technical idea of the invention, the medicinal powder is selected from at least one of metformin and its excipient.

In one embodiment of the invention, the thick colloidal layer 10 of the tablet 100 is composed of a mixture of the filler, the diluent, the excipient, the binder, the slow-release agent, and the sweetener.

In one embodiment of the invention, the powder colloidal layer 20 of the tablet 100 is composed of a mixture of the filler, the diluent, the excipient, the binder, the slow-release agent, the sweetener, and the medicine powder.

In one embodiment of the invention, further comprising at least one of disintegrant and lubricant.

Figure 2:
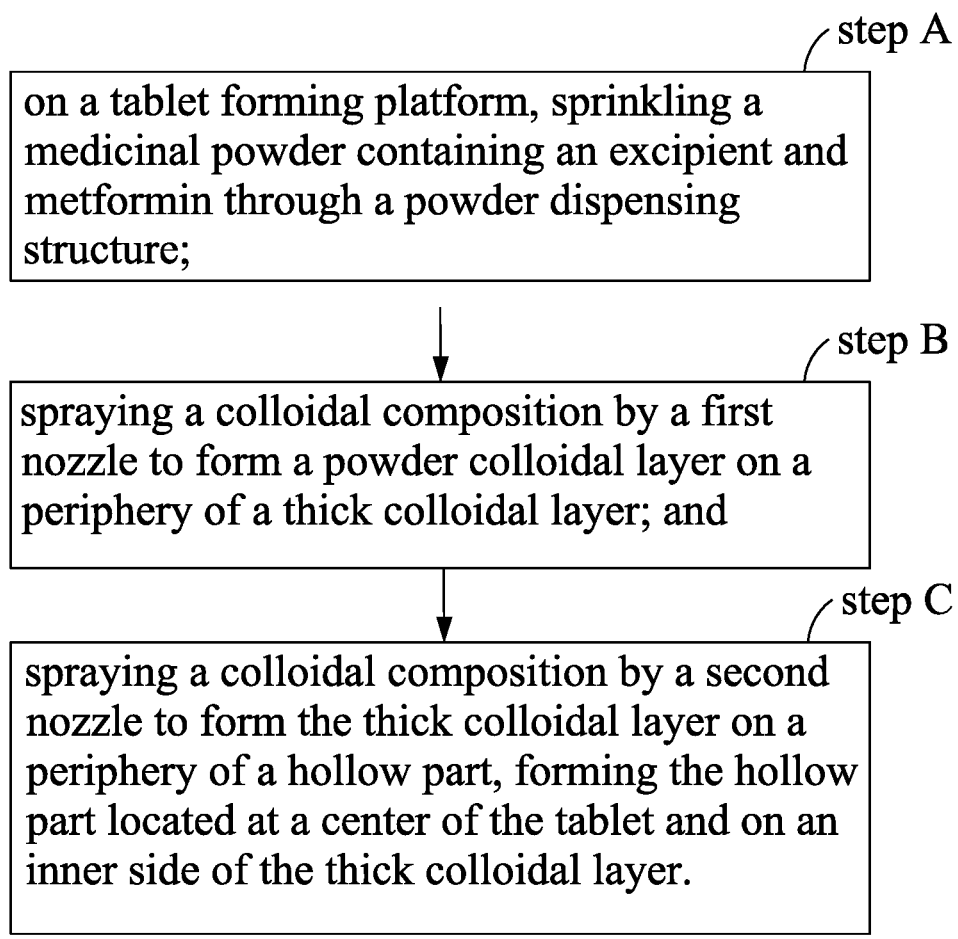
FIG. 2 is a flow chart showing implementation steps of a manufacturing method of a metformin tablet for relieving pain and reducing inflammation according to one embodiment of the invention.

Then, a manufacturing method of a metformin tablet for relieving pain and reducing inflammation of the invention will be described. Please refer to FIG. 1 and FIG. 2. FIG. 2 is a flow chart showing implementation steps of the manufacturing method of the metformin tablet for relieving pain and reducing inflammation according to one embodiment of the invention.

As shown in FIG. 2, the manufacturing method of the metformin tablet 100 for relieving pain and reducing inflammation of the invention comprises step A: on a tablet forming platform, sprinkling a medicinal powder containing an excipient and metformin through a powder dispensing structure; step B: spraying a colloidal composition by a first nozzle to form a powder colloidal layer 20 on a periphery of a thick colloidal layer 10; and step C: spraying a colloidal composition by a second nozzle to form the thick colloidal layer 10 on a periphery of a hollow part 30; forming the hollow part 30 located at a center of the tablet 100 and on an inner side of the thick colloidal layer 10; wherein the excipient comprises at least one of PVP, PEG, and polymer; the medicinal powder comprises at least one of metformin and its excipient.

In addition, since a dosage of analgesics varies greatly among different patients, the conventional manufacturing process is not easy to adjust between batches, and a number of tablets in each batch will be large. A dosage of the metformin tablet 100 can be easily adjusted between batches during a manufacturing process, which enables patients to take the drug more accurately, and to reduce various side effects through accurate and effective doses to achieve an effect of pain relief.

In addition, according to a technical idea of the invention, an order of the step A, the step B, and the step C is not particularly limited, for example, the step A, the step B, and the step C are performed cyclically through the above method according to a required drug dosage.

In addition, in one embodiment of the invention, the first nozzle and the second nozzle spray to form the thick colloidal layer 10 and the powder colloidal layer 20 respectively by surrounding a center of the hollow part 30 in a swirl manner.

In addition, in one embodiment of the invention, a hole diameter of the first nozzle is smaller than a hole diameter of the second nozzle.

For example, in a specific embodiment of the manufacturing method of the metformin tablet 100 of the invention, the powder containing the excipient and metformin that have been well mixed can be evenly spread on a tablet forming platform (not shown in the figures) through a tablet manufacturing device (not shown in the figures), the manufacturing device is provided with the first nozzle with a small hole diameter, the second nozzle with a large hole diameter, and the tablet forming platform, a colloid is sprayed by using the first nozzle with a small hole diameter, and the colloid is bonded with the powder to form the powder colloidal layer 20. At this time, the powder colloidal layer 20 and the thick colloidal layer 10 are formed by spraying through the first nozzle and the second nozzle with different hole diameters to form the metformin tablet 100 with the hollow part 30.

In addition, in one embodiment of the invention, the manufacturing method of the metformin tablet 100 can be performed from an inner side towards an outer side in a vortex shape. For example, firstly, the second nozzle with a large hole diameter is used to spray a colloidal with a large hole diameter on an inner ring to form the thick colloidal layer 10; when the thick colloidal layer 10 is almost completed, then the medicinal powder is dispensed downward. Since a lower layer still has a colloidal with a small hole diameter and the thick colloidal layer 10, the fallen medicinal powder is also capable of adhering to the thick colloidal layer 10 and other areas other than the thick colloidal layer 10. After the medicinal powder has dispensed downward, a colloidal with a small hole diameter is sprayed, repeat the above steps until stacking reaches the hollow part 30, and then return to the above steps. In this way, the metformin tablet 100 comprising the thick colloidal layer 10, the powder colloidal layer 20 and the hollow part 30 can be formed.

Therefore, in addition to being capable of making the tablet smaller by mouth-dissolving before entering a gastro-intestinal tract and providing required slow-release properties, the metformin tablet 100 for relieving pain and reducing inflammation of the invention is also capable of enhancing an activation effect of AMPK, reducing a dosage, and reducing fluctuation of blood sugar in a patient, thereby enhancing a pain relief effect.

The embodied modes of the present invention are described above through the specific embodiments, and those skilled in the art can easily understand other advantages and efficacies of the present invention from the contents disclosed in this specification. However, it should be understood that the present invention can also be implemented or applied through other different specific embodied modes, and the details in this specification can also be modified or changed based on different viewpoints and applications without departing from the spirit of the present invention; for example, the various technical contents illustrated in the foregoing embodiments are combined or changed to form new embodied modes, and these embodied modes are of course regarded as a part of the contents of the present invention. Therefore, the scope of protection in the present invention also includes the following claims and the scope defined by them.

What is claimed is:

1. A metformin tablet for relieving pain and reducing inflammation, comprising:
   a filler comprising microcrystalline cellulose and silicified microcrystalline cellulose;
   a diluent comprising mannitol and a sugar alcohol;
   an excipient comprising polyvinylpyrrolidone (PVP) and polyethylene glycol (PEG);
   a binder comprising glucose and lactose;
   a slow-release agent comprising at least one of polylactic acid;
   a sweetener comprising isomalt;
   a medicinal powder comprising metformin and the excipient;
   a disintegrant; and
   a lubricant;
   wherein the metformin tablet comprises a hollow part, a first colloidal layer formed on an outer surface of the hollow part, and a second colloidal layer formed on an outer surface of the first colloidal layer;

wherein the first colloidal layer is thicker than the second colloidal layer, and is composed of a mixture of the filler having 2% to 22% by weight of the first colloidal layer, the diluent having 3% to 24% by weight of the first colloidal layer, the excipient having 1% to 25% by weight of the first colloidal layer, the binder having 0.5% to 18% by weight of the first colloidal layer, the slow-release agent having 0.1% to 12% by weight of the first colloidal layer, and the sweetener having 1% to 22% by weight of the first colloidal layer; and the second colloidal layer of the tablet is composed of a mixture of the filler having 2% to 22% by weight of the second colloidal layer, the diluent having 3% to 24% by weight of the second colloidal layer, the excipient having 1% to 25% by weight of the second colloidal layer, the binder having 0.5% to 18% by weight of the second colloidal layer, the slow-release agent having 0.1% to 12% by weight of the second colloidal layer, the sweetener having 1% to 22% by weight of the second colloidal layer, and the medicinal powder.

\* \* \* \* \*